(12) United States Patent
Masuda et al.

(10) Patent No.: US 8,419,456 B2
(45) Date of Patent: Apr. 16, 2013

(54) CONTACT MEMBER FOR A GAS SENSOR, METHOD FOR CONNECTING A CONTACT MEMBER WITH A SENSOR ELEMENT IN A GAS SENSOR, AND METHOD FOR MANUFACTURING A GAS SENSOR

(75) Inventors: Koichi Masuda, Nagoya (JP);
Nobukazu Ikoma, Nagoya (JP);
Hirohito Kiyota, Kiyosu (JP)

(73) Assignee: NGK Insulators, Ltd., Nagoya (JP)

( * ) Notice: Subject to any disclaimer, the term of this patent is extended or adjusted under 35 U.S.C. 154(b) by 14 days.

(21) Appl. No.: 13/279,853

(22) Filed: Oct. 24, 2011

(65) Prior Publication Data

US 2012/0071042 A1 Mar. 22, 2012

Related U.S. Application Data

(63) Continuation of application No. PCT/JP2011/056743, filed on Mar. 22, 2011.

(30) Foreign Application Priority Data

Mar. 31, 2010 (JP) ................................. 2010-080456

(51) Int. Cl.
*H01R 9/09* (2006.01)
(52) U.S. Cl.
USPC ........................... 439/263; 439/593; 439/932
(58) Field of Classification Search ................... 439/263, 439/593, 932, 592
See application file for complete search history.

(56) References Cited

U.S. PATENT DOCUMENTS

| | | | |
|---|---|---|---|
| 2001/0025522 A1 | 10/2001 | Kojima | |
| 2004/0040370 A1 | 3/2004 | Kojima | |
| 2004/0137777 A1* | 7/2004 | Fukuda | 439/349 |
| 2005/0054221 A1* | 3/2005 | Mayer et al. | 439/76.1 |
| 2009/0101503 A1 | 4/2009 | Kanao | |
| 2011/0197666 A1* | 8/2011 | Cheng et al. | 73/114.19 |

FOREIGN PATENT DOCUMENTS

| | | |
|---|---|---|
| JP | 11-248671 A1 | 9/1999 |
| JP | 2001-343356 A1 | 12/2001 |
| JP | 2002-168822 A1 | 6/2002 |
| JP | 2002-168824 A1 | 6/2002 |
| JP | 2004-093302 A1 | 3/2004 |
| JP | 2006-284223 A1 | 10/2006 |
| JP | 2009-115784 A1 | 5/2009 |

* cited by examiner

*Primary Examiner* — Gary F. Paumen
(74) *Attorney, Agent, or Firm* — Burr & Brown

(57) ABSTRACT

In a contact member for a gas sensor configured to fix a sensor element by sandwiching the sensor element in an insertion port defined by a pair of housing members to thereby obtain electrical connection with the sensor element, a restraint member provided at an outer circumference of the pair of housing members and having a restraint function for restraining a displacement of the pair of housing members within a predetermined range is used. The restraint member includes: two pressing surface portions to which a compression force that occurs when the annular member shrinkingly deforms is applied; a first side portion coupled perpendicularly to the two pressing surface portions; and a second side portion having an upper side portion coupled perpendicularly to one of the pressing surface portions and a lower side portion coupled perpendicularly to the other of the pressing surface portions.

4 Claims, 13 Drawing Sheets

F I G. 6
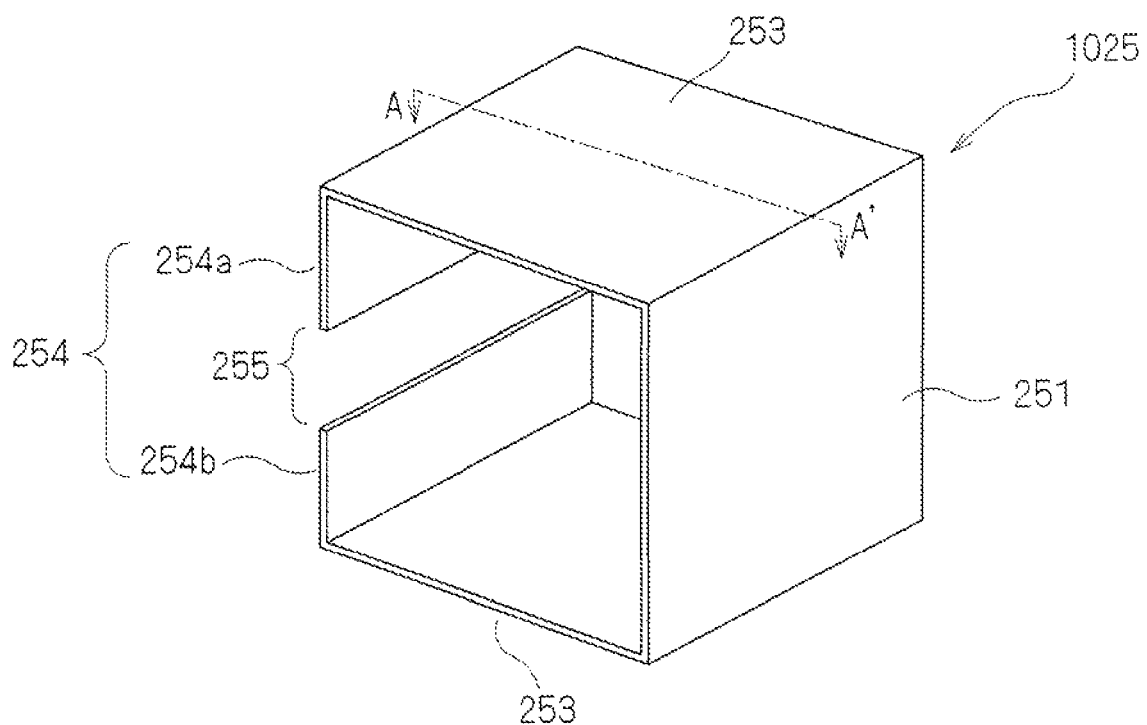

F I G . 1 1
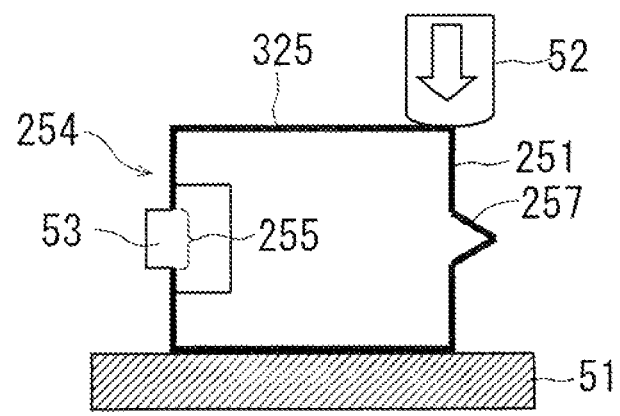

F I G . 1 2
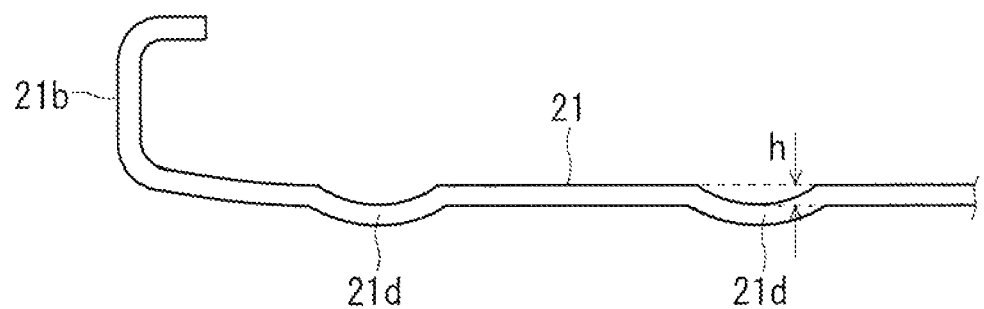

CONTACT MEMBER FOR A GAS SENSOR, METHOD FOR CONNECTING A CONTACT MEMBER WITH A SENSOR ELEMENT IN A GAS SENSOR, AND METHOD FOR MANUFACTURING A GAS SENSOR

TECHNICAL FIELD

The present invention relates to a gas sensor for measuring a concentration of a predetermined gas component in a measurement gas, and particularly relates to a technique for holding and fixing a sensor element thereof.

BACKGROUND ART

Conventionally, various measuring apparatuses have been used for recognizing a concentration of a desired gas component in a measurement gas. For example, as a device for measuring a NOx concentration in a measurement gas such as a combustion gas, known is a gas sensor (NOx sensor) having oxygen-ion conductivity, such as one made constituted by zirconia ($ZrO_2$) (for example, see Patent Document 1). In such a gas sensor, in general, a sensor element has a plurality of electrode terminals formed on a surface thereof for applying a voltage, retrieving a detection signal, supplying power to a heater part, and the like.

Here, the gas sensor includes a contact member for holding the sensor element inserted therein. For example, a gas sensor is already known having a contact member that includes: a housing in which an insertion port for insertion of a sensor element is defined by a pair of housing members arranged opposed to each other; a plurality of contact-point members configured as metal terminals provided on the housing member; and a plurality of lead wires connected to the contact-point members for electrical conduction between the sensor element and the outside (for example, see Patent Document 2).

In the gas sensor disclosed in the Patent Document 2, the contact member holds the sensor element inserted in the insertion port while making the contact-point members and electrode terminals in contact with each other, thereby obtaining electrical conduction between the sensor element and the outside. In other words, in the gas sensor disclosed in the Patent Document 2, the contact-point members serve as contact points with the electrode terminals. Specifically, in a state where the sensor element is inserted in the insertion port, the housing members are fitted into a fixture having a substantially concave shape (or substantially C-like shape) in a cross-sectional view and having pressure springs formed at upper and lower sides thereof, and additionally a clamping ring is arranged at an outer circumferences of the fixture and the pressure springs and then the clamping ring is clamped so that the pressure springs are displaced to bias the contact-point members to the electrode terminals due to an elastic force of the pressure springs, thus holding the sensor element and ensuring the electrical conduction.

Here, the fixture disclosed in the. Patent Document 2 not only serves to fix a spring member as described above but also serves to restrain the pair of housing members in a predetermined positional relationship until the sensor element is inserted in the insertion port and the clamping ring is clamped. This restraint is necessary for achieving a correct contact between each electrode terminal and a corresponding contact-point member without misalignment at the time of holding and fixing the sensor element between the pair of housing members (that is, in the insertion port) by clamping the clamping ring. In a case of the Patent Document 2, since the fixture has a concave shape in a cross-sectional view, an elasticity of the fixture serving as a leaf spring is utilized for holding and restraining the housing members.

In the gas sensor disclosed in the Patent Document 2, the clamping ring is clamped so that the elastic force of the pressure springs is applied to the housing via the fixture, thereby fixing the sensor element to the housing. At this time, the contact-point members provided on the housing bias the electrode terminals, and thereby the contact between the electrode terminals and the contact-point members is ensured.

Here, however, a problem arises that a force acting on the housing may be asymmetric (non-uniform) because the fixture has a concave shape in a cross-sectional view as described above. In a gas sensor configured to have a plurality of electrode terminals in contact with corresponding contact-point members, respectively, a biasing force of the contact-point member to the electrode terminal varies depending on positions due to the non-uniformity, which may consequently cause a local contact failure.

PRIOR-ART DOCUMENTS

Patent Documents

Patent Document 1: Japanese Patent Application Laid-Open No. 2006-284223
Patent Document 2: Japanese Patent Application Laid-Open No. 2002-168822

SUMMARY OF THE INVENTION

The present invention is made in view of the problem described above, and an object of the present invention is to provide a gas sensor capable of stably ensuring electrical conduction between a sensor element and a contact member.

To solve the above-described problem, in a fist aspect of the present invention, a contact member for a gas sensor configured to fix a sensor element by sandwiching the sensor element in an insertion port defined by a pair of housing members to thereby obtain electrical connection with the sensor element, the contact member includes: a restraint member provided at an outer circumference of the pair of housing members, the restraint member having a restraint function for restraining a displacement of the pair of housing members within a predetermined range; and an annular member provided at an outer circumference of the restraint member. A compression force, which occurs when the annular member shrinkingly deforms by receiving an external force with the sensor element inserted in the insertion port, is applied through the restraint member to thereby contact the pair of housing members with the sensor element under pressure, so that the sensor element is fixed by being sandwiched between the pair of housing members in a state that an electrode terminal provided on the sensor element and a contact-point member provided on the pair of housing members are in contact with each other. The restraint member includes: two pressing surface portions to which the compression force that occurs when the annular member shrinkingly deforms is applied; a first side portion coupled perpendicularly to the two pressing surface portions; and a second side portion having an upper side portion coupled perpendicularly to one of the two pressing surface portions and a lower side portion coupled perpendicularly to the other of the two pressing surface portions, the second side portion also having a spaced portion provided between the upper side portion and the lower side portion. The first side portion has a reaction-force suppressing structure for suppressing occurrence of a reaction force reactive to the compression force.

In a second aspect of the present invention, in the contact member for a gas sensor according to the fist aspect, the first side portion has at least one opening, and the reaction force is suppressed by causing an end edge portion located lateral to the opening to compressively deform due to the compression force.

In a third aspect of the present invention, in the contact member for a gas sensor according to the fist aspect, the first side portion has a bent portion, and the reaction force is suppressed by causing the bent portion to compressively deform due to the compression force.

In a fourth aspect of the present invention, in the contact member for a gas sensor according to the fist aspect, the first side portion has at least one opening and also has a bent portion formed at an end edge portion located lateral to the opening, and the reaction force is suppressed by causing the end edge portion including the bent portion to compressively deform.

In a fifth aspect of the present invention, a method for connecting a contact member with a sensor element in a gas sensor includes the steps of: preparing a contact member, the contact meter including a pair of housing member arranged so as to define an insertion port for insertion of the sensor element, a restraint member provided at an outer circumference of the pair of housing members, the restraint member having a restraint function for restraining a displacement of the pair of housing members within a predetermined range, and an annular member provided at an outer circumference of the restraint member; inserting the sensor element into the insertion port; and applying an external force to the annular member to cause the annular member to shrinkingly deform to thereby contact the pair of housing members with the sensor element under pressure, so that the sensor element is fixed by being sandwiched between the pair of housing members in a state that an electrode terminal provided on the sensor element and a contact-point member provided on the pair of housing members are in contact with each other. The restraint member includes: two pressing surface portions to which a compression force that occurs when the annular member shrinkingly deforms is applied; a first side portion coupled perpendicularly to the two pressing surface portions; and a second side portion having an upper side portion coupled perpendicularly to one of the two pressing surface portions and a lower side portion coupled perpendicularly to the other of the two pressing surface portions, the second side portion also having a spaced portion provided between the upper side portion and the lower side portion. The first side portion has a reaction-force suppressing structure for suppressing occurrence of a reaction force reactive to the compression force.

In an sixth aspect of the present invention, in the method for connecting a contact member with a sensor element according to the fifth aspect, the first side portion has at least one opening, and the reaction force is suppressed by causing an end edge portion located lateral to the opening to compressively deform due to the compression force.

In an seventh aspect of the present invention, in the method for connecting a contact member with a sensor element according to the fifth aspect, the first side portion has a bent portion, and the reaction force is suppressed by causing the bent portion to compressively deform due to the compression force.

In a eighth aspect of the present invention, in the method for connecting a contact member with a sensor element according to the fifth aspect, the first side portion has at least one opening and also has a bent portion formed at an end edge portion located lateral to the opening, and the reaction force is suppressed by causing the end edge portion including the bent portion to compressively deform.

In an ninth aspect of the present invention, a method for manufacturing a gas sensor includes the steps of: arranging a pair of housing members so as to define an insertion port for insertion of a sensor element; providing a restraint member at an outer circumference of the pair of housing members, the restraint member having a restraint function for restraining a displacement of the pair of housing members within a predetermined range; providing an annular member at an outer circumference of the restraint member; inserting the sensor element into the insertion port; and applying an external force to the annular member to cause the annular member to shrinkingly deform to thereby contact the pair of housing members with the sensor element under pressure, so that the sensor element is fixed by being sandwiched between the pair of housing members in a state that an electrode terminal provided on the sensor element and a contact-point member provided on the pair of housing members are in contact with each other. The restraint member includes: two pressing surface portions to which a compression force that occurs when the annular member shrinkingly deforms is applied; a first side portion coupled perpendicularly to the two pressing surface portions; and a second side portion having an upper side portion coupled perpendicularly to one of the two pressing surface portions and a lower side portion coupled perpendicularly to the other of the two pressing surface portions, the second side portion also having a spaced portion provided between the upper side portion and the lower side portion. The first side portion has a reaction-force suppressing structure for suppressing occurrence of a reaction force reactive to the compression force.

In a tenth aspect of the present invention, in the method for manufacturing a gas sensor according to the ninth aspect, the first side portion has at least one opening, and the reaction force is suppressed by causing an end edge portion located lateral to the opening to compressively deform due to the compression force.

In a eleventh aspect of the present invention, in the method for manufacturing a gas sensor according to the ninth aspect, the first side portion has a bent portion, and the reaction force is suppressed by causing the bent portion to compressively deform due to the compression force.

In a twelfth aspect of the present invention, in the method for manufacturing a gas sensor according to the ninth aspect, the first side portion has at least one opening and also has a bent portion formed at an end edge portion located lateral to the opening, and the reaction force is suppressed by causing the end edge portion including the bent portion to compressively deform.

According to the first to twelfth aspects of the present invention, in the restraint member, the reaction-force suppressing structure is provided at the first side portion to which the compression force is applied from upper and lower sides thereof at a time of clamping. This suppresses occurrence of a slanted load in the contact-point member of the contact member, and therefore a uniform and stable contact state can be established between the contact-point member of the contact member and the electrode terminal of the sensor element.

BRIEF DESCRIPTION OF THE DRAWINGS

FIG. 6 is a perspective view showing a main part of a conventional fixture 1025.

FIG. 11 is a diagram schematically showing measurement of the deformation behavior of the fixture.

FIG. 12 is a diagram showing the height h of a protrusion 21d.

FIG. 14 is a diagram showing a normal probability density curve of a difference Δw between left and right opening degrees of housing members 24a.

EMBODIMENT FOR CARRYING OUT THE INVENTION

<Outline Structure of Gas Sensor>

Figure 1A:
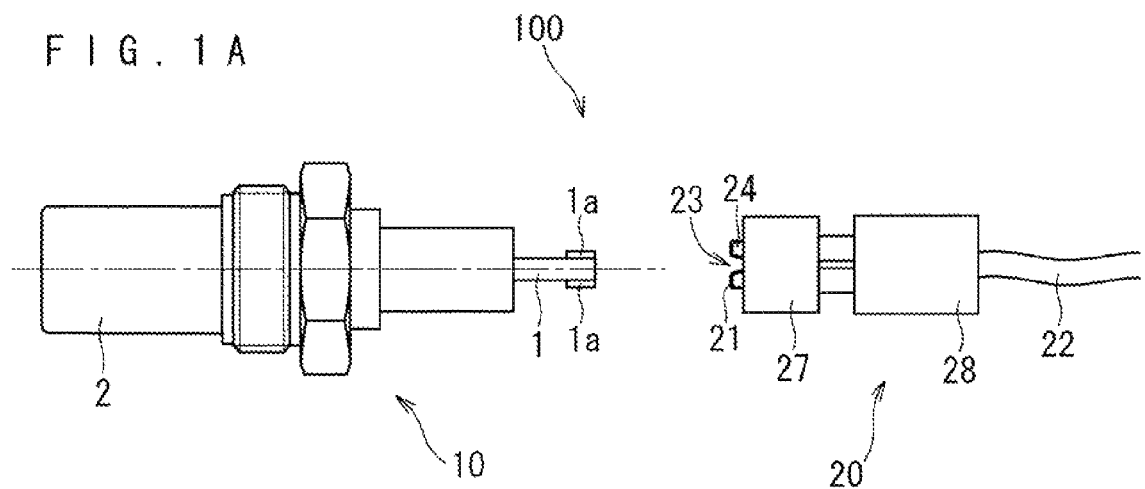
FIGS. 1A and 1B are diagrams showing assembling of a gas sensor 100.
Figure 1B:
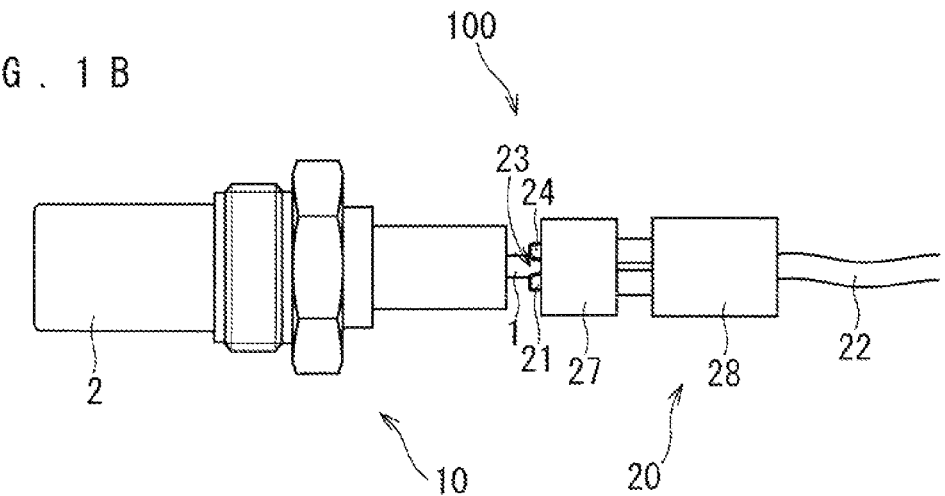

Firstly, an outline structure of a gas sensor 100 will be described. The gas sensor 100 is for detecting a predetermined gas component (objective gas component) in a gas (measurement gas) to be measured, and further measuring a concentration thereof. FIGS. 1A and 1B are diagrams showing the gas sensor 100 during assembling. FIG. 1A shows a state before the assembling, and FIG. 1B shows a state after the assembling.

The gas sensor 100 has a structure in which a gas sensor main body 10 and a contact member 20 are integrated. The gas sensor main body 10 includes a sensor element I serving as a gas detection part, and a reception member 2 for receiving the sensor element 1. On the other hand, the contact member 20 mainly includes a plurality of contact-point members 21, lead wires 22 connected to the contact-point members 21, a ceramic-made housing 24 for holding the sensor element 1 inserted in an insertion port 23 with interposition of the contact-point members 21, and a grommet 28 formed so as to allow the lead wires 22 to be air-tightly inserted therethrough.

As shown in FIG. 1B, the sensor element 1 included in the gas sensor main body 10 is inserted in the insertion port 23 of the housing 24 included in the contact member 20, and additionally the sensor element 1 is held in the housing 24 with interposition of the contact-point members 21, thereby forming the gas sensor 100 as an integrated part.

Figure 2:
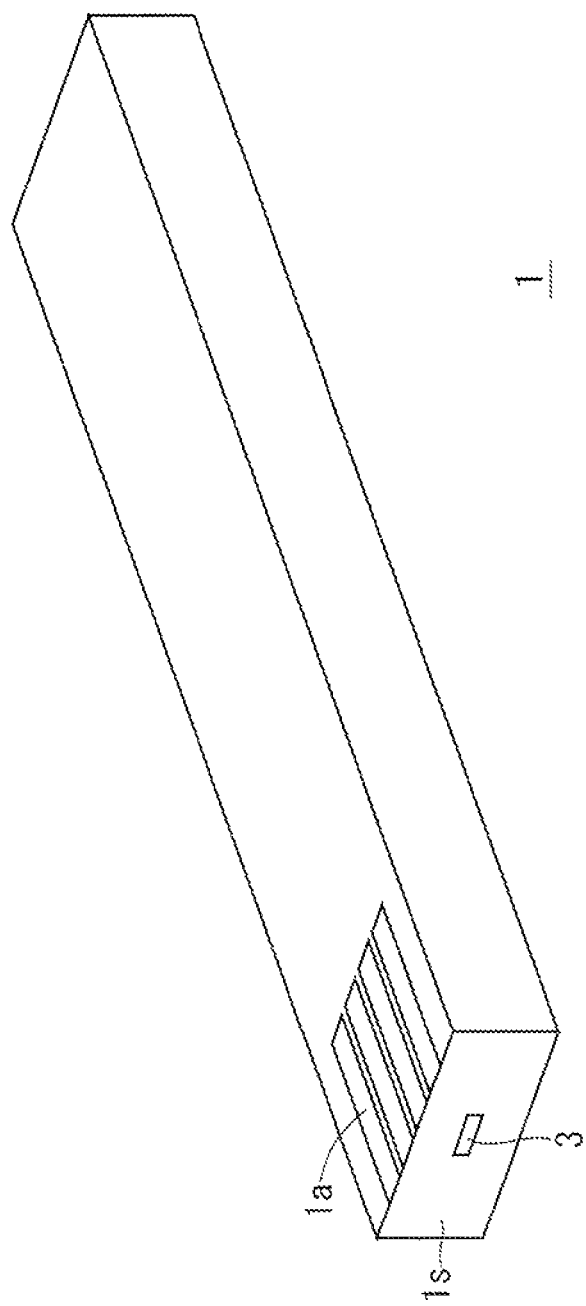
FIG. 2 is a perspective view showing an outer shape of a sensor element 1.

FIG. 2 is a perspective view showing an outer shape of the sensor element 1. The sensor element 1 has a structure in which a plurality of oxygen-ion conductive solid electrolyte layers such as zirconia ($ZrO_2$) layers are laminated. The sensor element 1 has, on a surface and a back surface thereof, a plurality of electrode terminals 1a for applying a voltage, retrieving a detection signal, supplying power to a heater part, and the like. In the sensor element 1 shown in FIG. 2, four electrode terminals 1a are provided at one side (the electrode terminals 1a provided on the back surface are not shown). However, this is merely illustrative, and the number of electrode terminals 1a may be appropriately set in accordance with a structure of the sensor element 1. In the sensor element 1, a gas inlet 3 for introducing a reference gas is provided in an end face Is at the side where the electrode terminals 1a are provided, and a measurement gas inlet (not shown) is provided in the other end.

The sensor element 1 is manufactured by, for example, performing a predetermined process and printing a pattern of electrodes and circuits on ceramic green sheets, each of which corresponds to each of the layers, then laminating the green sheets, cutting a resulting laminated body into a predetermined size, and then baking a resulting laminated body. In the gas sensor 100, the objective gas component is detected by utilizing the fact that a current corresponding to the amount of objective gas component in the measurement gas flows between predetermined electrodes at a time of introducing the measurement gas into the sensor element 1.

<Detailed Configuration of Contact Member>

Figure 3:
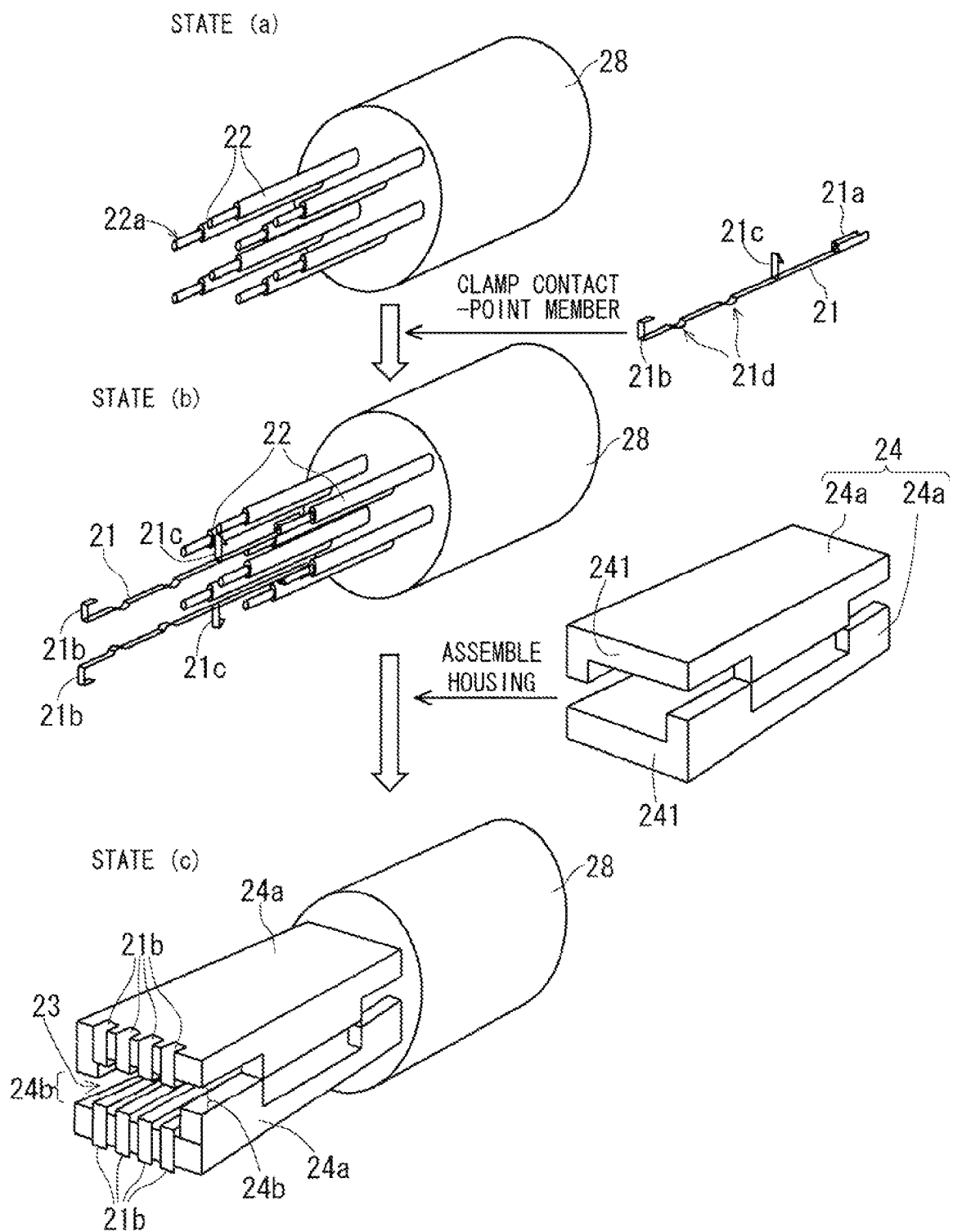
FIG. 3 is a diagram schematically showing a process of assembling a contact member 20.
Figure 4:
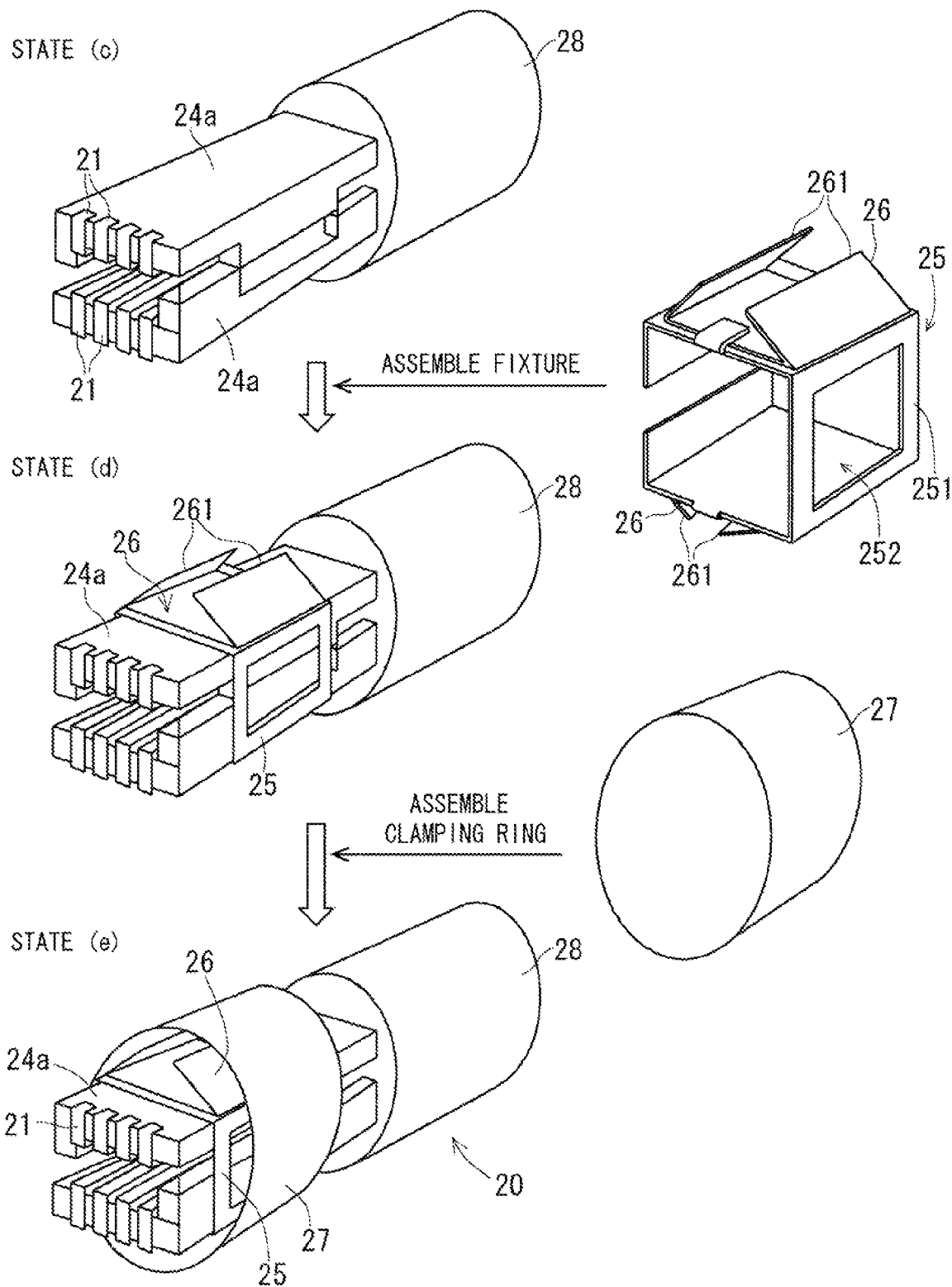
FIG. 4 is a diagram schematically showing the process of assembling the contact member 20.

Next, a detailed configuration of the contact member 20 will be described with showing an assembling process thereof. FIGS. 3 and 4 are diagrams schematically showing a process of assembling the contact member 20. This process of assembling the contact member 20 is preliminary performed before the gas sensor main body 10 and the contact member 20 are integrated with each other. In this sense, the process of assembling the contact member 20 will be referred to as "pre-assembling process" and this assembling will be also referred to as "pre-assembling".

In the pre-assembling of the contact member 20, firstly, the lead wires 22 are inserted through the grommet 28, as shown in a state (a) of FIG. 3. Then, as shown in a state (b), a pressure-bonding portion 21a of the contact-point member 21 is connected to a distal end portion 22a of each lead wire 22. This connection is achieved by clamping the pressure-bonding portion 21a from the outside while the distal end portion 22a of the lead wire 22 is sandwiched in the pressure-bonding portion 21a. In the state (b), for simplification of the illustration, the contact-point members 21 are connected to only two lead wires 22, but actually, the contact-point members 21 are connected to all of the lead wires 22.

After the contact-point members 21 are connected, then the housing 24 is assembled as shown in a state (c) of FIG. 3. In more detail, the housing 24 includes a pair of housing members 24a arranged opposed to each other, and the assembling of the housing 24 is achieved by a first latch portion 21b and a second latch portion 21c of the contact-point member 21 being latched to predetermined positions in the housing members 24a.

More specifically, the first latch portion 21b is latched to a first latched portion 241 provided at one end portion of the housing member 24a. Therefore, the shapes of the first latch portion 21b and the first latched portion 241 are determined such that their latch state can be successfully maintained. That is, the first latch portion 21b is formed into a shape that matches a side-cross-sectional shape of the first latched portion 241. On the other hand, the second latch portion 21c is inserted and fitted into a second latched portion (not shown) provided in a middle portion of the housing member 24a, and thereby latched to the housing member 24a.

Here, the housing members 24a have substantially the same cross-sectional shape, and in assembling, they are spaced apart from each other such that a space having a rectangular shape in a cross-sectional view can be formed therebetween to serve as the insertion port 23. For this purpose, a gap 24b is formed at end portions of the two housing members 24a. In other words, the housing members 24a are shaped as if a housing defining a space therein and having a rectangular shape in a cross-sectional shape is divided into two pieces. Assembling in the above-described manner enables a distal end portion and its neighborhood (near an end portion of the insertion port 23) of each housing member 24a to be deviated upward or downward within a predetermined range when an external force acting from the inside of the insertion port 23 toward the upper or lower side of the drawing sheet of FIG. 3. The pair of housing members 24a receive the external force to sandwich the sensor element 1 in the insertion port 23, and thus the sensor element 1 is fixed to the contact member.

In assembling the housing 24, as shown in a state (d) of FIG. 4, a fixture 25 having pressure springs 26 fixed thereto in advance is also assembled to the outside of the housing 24.

The pressure spring 26 is a leaf spring member shaped into a trapezoidal shape having no upper base in a cross-sectional view. When the external force is applied to a free end 261 of the pressure spring 26, the pressure spring 26 generates an elastic force as its resilient force.

The fixture 25 not only serves to fix the pressure springs 26 but also serves to maintain a state where the housing 24 is assembled and more specifically a state where the insertion port 23 is formed, until the sensor element 1 is fixed in a sandwiched manner. In other words, the fixture 25 is a restraint member for restraining the pair of housing members 24a within a predetermined position range such that the state where the insertion port 23 is formed can be maintained. Assembling the fixture 25 together with the housing 24 can prevent occurrence of misalignment between the each contact-point member 21 (and more specifically a protrusion 21d) and a corresponding electrode terminal 1a of the sensor element 1 when the sensor element 1 is fixed. That is, it can be considered that the fixture 25 also serves to restrain the position range of the sensor element 1 at a time of fixing and sandwiching.

In the gas sensor 100 according to this embodiment, the fixture 25 has a characteristic structure. Details of the fixture 25 will be described later.

After the fixture 25 is assembled, a clamping ring 27 which is an annular (cylindrical) member is assembled, as shown in a state (e). Through the above-described steps, the pre-assembling is completed. Thus, the state (e) shows a state after the contact member 20 is assembled.

The clamping ring 27 is clamped after the pre-assembling and at a time of integrating the gas sensor main body 10 and the contact member 20 with each other, while the sensor element 1 is inserted in the insertion port 23 of the housing 24. In other words, the clamping ring 27 is shrinkingly deformed by an external force. As a result, a gap of the insertion port 23 of the housing 24 is reduced so that the sensor element 1 is biased from two directions, that is, from upper and lower sides thereof, due to the contact-point members 21 (and more specifically the protrusions 21d) included in the respective housing members 24a. Thus, a state where the sensor element 1 is fixed while being sandwiched between the pair of housing members 24a is achieved. At this time, the protrusion 21d of each contact-point member 21 is brought into contact with a corresponding electrode terminal 1a, and therefore electrical conduction between the sensor element 1 and the outside can be achieved through the lead wire 22 connected to the contact-point member 21.

<Detailed Configuration of Fixture>

The gas sensor 100 according to this embodiment is characterized by the structure of the fixture 25, as described above. A more specific description of a configuration of the fixture 25 will be given below.

Figure 5:
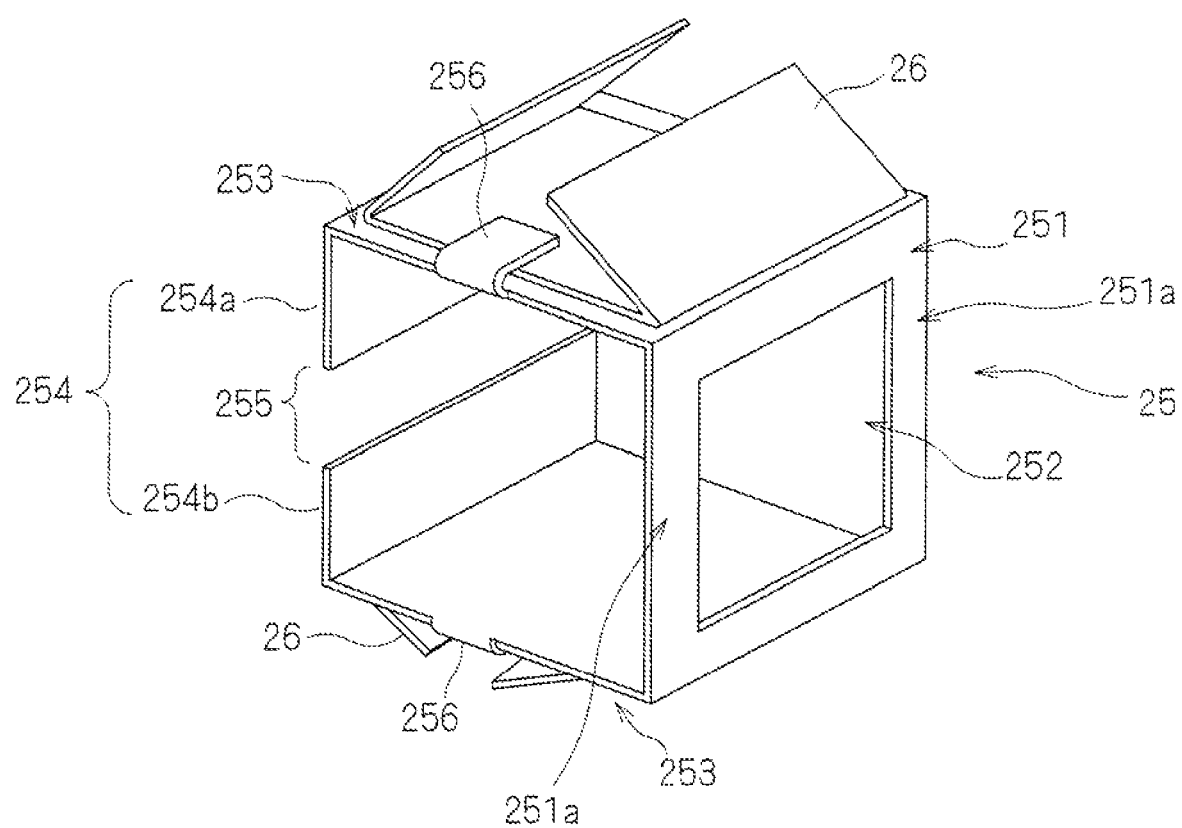
FIG. 5 is a perspective view showing a structure of a fixture 25 according to this embodiment.

FIG. 5 is a perspective view showing the structure of the fixture 25 according to this embodiment. In outline, the fixture 25 is configured as one piece including a first side portion 251 having a rectangular opening 252, two upper and lower pressing surface portions 253 coupled perpendicularly to the first side portion 251, and a second side portion 254 opposed to the first side portion 251. The second side portion 254 is divided into an upper side portion 254a and a lower side portion 254b, which have a spaced portion 255 interposed therebetween and each of which is coupled perpendicularly to each of the upper and lower pressing surface portions 253. In assembling the contact member 20, the housing member 24a is restrained by the fixture 25 while being surrounded by the first side portion 251, the two pressing surface portions 253, and the second side portion 254.

The opening 252 is formed such that its area ratio to the entire first side portion 251 is not less than 0.22. In such a case, after the clamping ring 27 is clamped, a state is achieved in which the sensor element 1 is uniformly sandwiched and fixed by the pair of housing members 24a (in more detail, by the contact-point members 21 latched to the housing members 24a). If the area ratio is less than 0.22, an effect of providing the opening 252 (details thereof will be described later) cannot be suitably obtained. No particular limitation is put on an upper limit of the area ratio of the opening 252 to the entire first side portion 251, as long as it is within a range that allows the two pressing surface portions 253 to be kept perpendicular to the first side portion 251 and that does not hinder the assembling of the fixture 25, Additionally, the upper limit varies depending on a material of the fixture 25.

Providing the opening 252 means, in other words, that the first side portion 251 is continuous with the two upper and lower pressing surface portions 253 only in two end edge portions 251a provided at left and right sides of the opening 252.

Since the first side portion 251 and the second side portion 254 have different shapes, it can be said that the two side portions of the fixture 25 are asymmetric.

In each of the pressing surface portions 253, the pressure spring 26 is held and fixed by a pair of holders 256 (only a part of which is shown in FIG. 5). In this embodiment, an extension portion extending out of the pressing surface portion 253 is preliminary provided at an end portion of the pressing surface portion 253, and the extension portion is folded to thereby make a lower base portion of the pressure spring 26 sandwiched between the pressing surface portion 253 and the extension portion, thus holding the pressure spring 26. However, how to hold the pressure spring 26 by the fixture 25 is not limited thereto.

It is necessary that the fixture 25 is made of a corrosion-resistant material (metal material). In terms of the strength of the material, it suffices that the strength is ensured to such a degree that the fixture 25 having the above-described structure can be suitably processed. Rather, from the viewpoint of suitably achieving a deformation behavior which will be described next, it is not necessary to adopt an excessively strong material. Although there is no specific restriction on the material, stainless steel (such as SUS304) may be mentioned as a preferable example. The fixture 25 can be prepared by, for example, performing a known processing technique such as a folding process and a drilling process on a single metal plate made of the stainless steel or the like.

<Deformation Behavior of Fixture and Fixing of Sensor Element>

Next, effects obtained by adopting the above-described configuration in the fixture 25 will be described. As will be detailed later, the effects are obtained in a phase of integrating the gas sensor main body 10 and the contact member 20 with each other.

FIG. 6 is a perspective view showing a main part of a conventional fixture 1025 for comparison. For simplification of the illustration, pressure springs and a part for holding them are not shown. The fixture 1025 shown in FIG. 6 has a configuration identical to that of the fixture 25 according to this embodiment, except that the opening 252 is not provided.

Figure 7A:
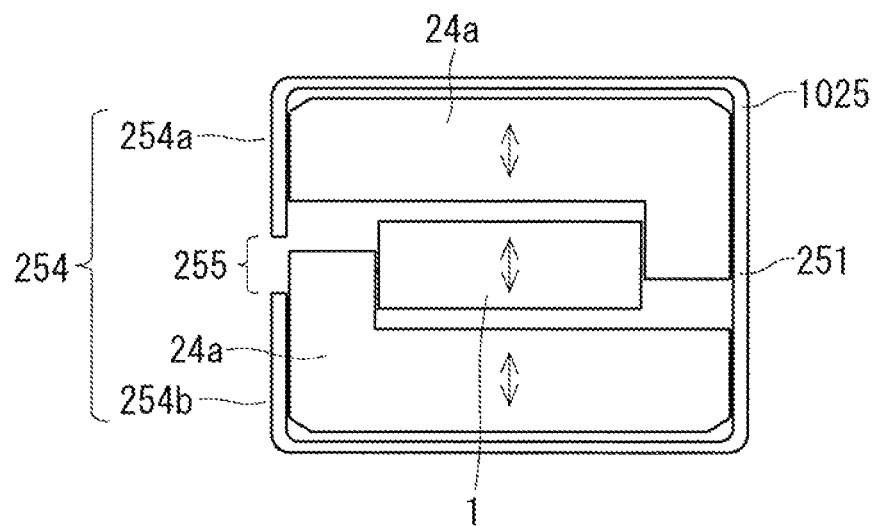
FIGS. 7A and 7B are cross-sectional views schematically showing the contact member 20 as taken along the line A-A' of FIG. 6.
Figure 7B:
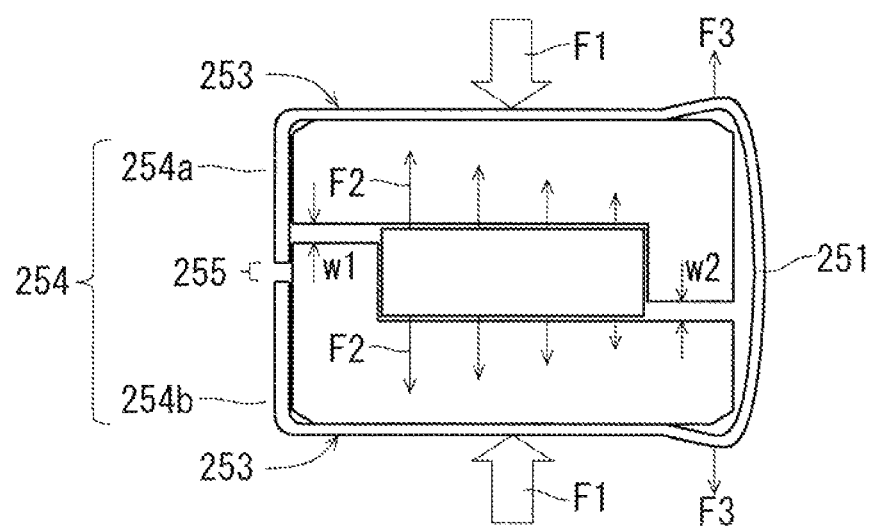

FIGS. 7A and 7B are a cross-sectional view schematically showing the contact member 20 as taken along the line A-A' of FIG. 6 before and after the clamping ring 27 is clamped, in a case where the contact member 20 is configured using the conventional fixture 1025. For simplification of the illustration, the contact-point members 21, the pressure springs 26, and the clamping ring 27 are not shown.

As shown in FIG. 7A, in a state before the clamping, the housing members 24a and the sensor element 1 are displaceable within a certain range (as indicated by the arrows in FIG. 7A) though the housing members 24a and the sensor element I are restrained by the fixture 1025.

If the clamping ring 27 is clamped so that an elastic force F1 is applied from the pressure springs 26 to the fixture 1025, as shown in FIG. 7B, the elastic force F1 occurring in the pressure springs 26 works as a force in a direction of compressing the fixture 1025, which acts on the two upper and lower pressing surface portions 253. At this time, in the second side portion 254 in which the upper side portion 254a and the lower side portion 254b are spaced apart from each other, no reaction force occurs and the spaced portion 255 is narrowed to bring the upper side portion 254a and the lower side portion 254b closer to each other.

On the other hand, the first side portion 251 is continuous with the two pressing surface portions 253, the first side portion 251 receives a compression force from two directions of the upper side and the lower side, so that the first side portion 251 deforms into a convex shape toward the outside of the fixture 1025, as shown in FIG. 7B.

As a result, after the clamping, the sensor element 1 is contacted and fixed under pressure by the contact-point members 21 in a state that a reaction force F3 reactive to the compressive deformation occurs near the first side portion 251 and the elastic force applied from the contact-point members 21 to the sensor element 1 and its resistance force F2 vary in the magnitude among the individual contact-point members 21. That is, a slanted-load state occurs in which non-uniform loads are applied to the individual contact-point members 21. In this slanted-load state, contacts between the contact-point members 21 and the electrode terminals 1a of the sensor element 1 are not uniform, and a contact-point failure may occur at the contact-point member 21 having the protrusion 21d thereof largely deformed because of an excessive load.

Additionally, such a slanted-load state may cause a significant difference between the left and right opening degrees (distances) w1 and w2 of the two housing members 24a after the clamping, though not shown in detail in FIG. 7B.

Figure 8:
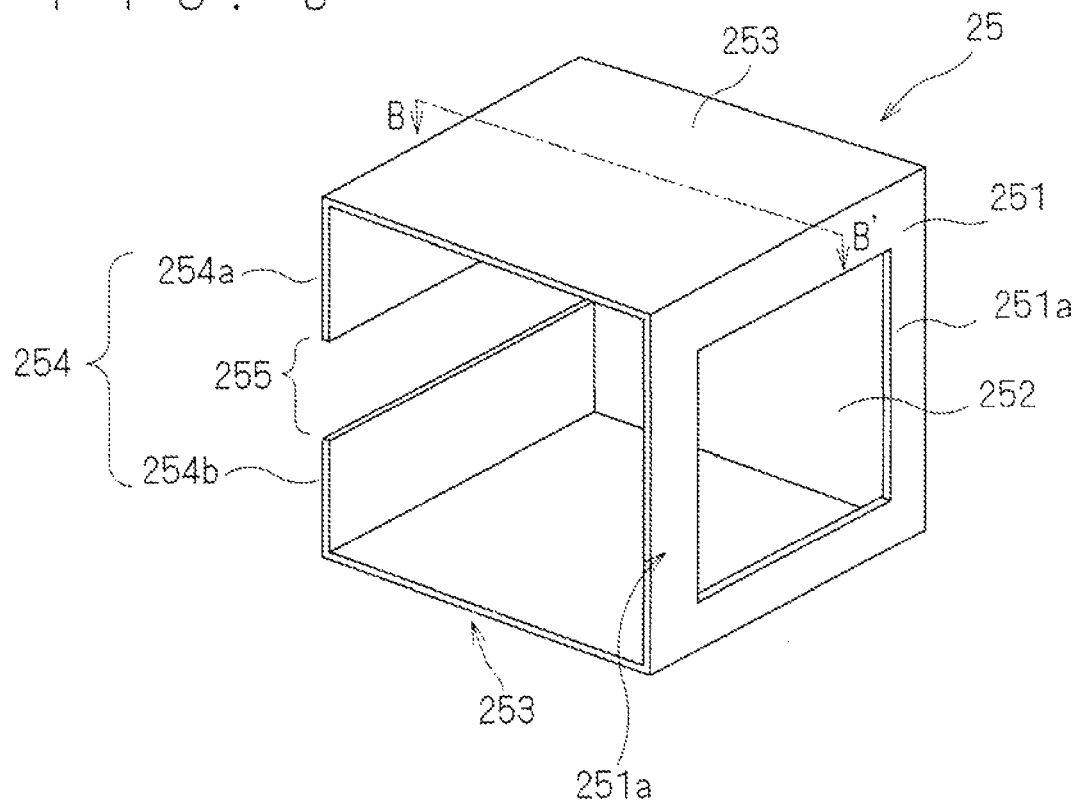
FIG. 8 is a perspective view showing a main part of the fixture 25 according to this embodiment.
Figure 9:
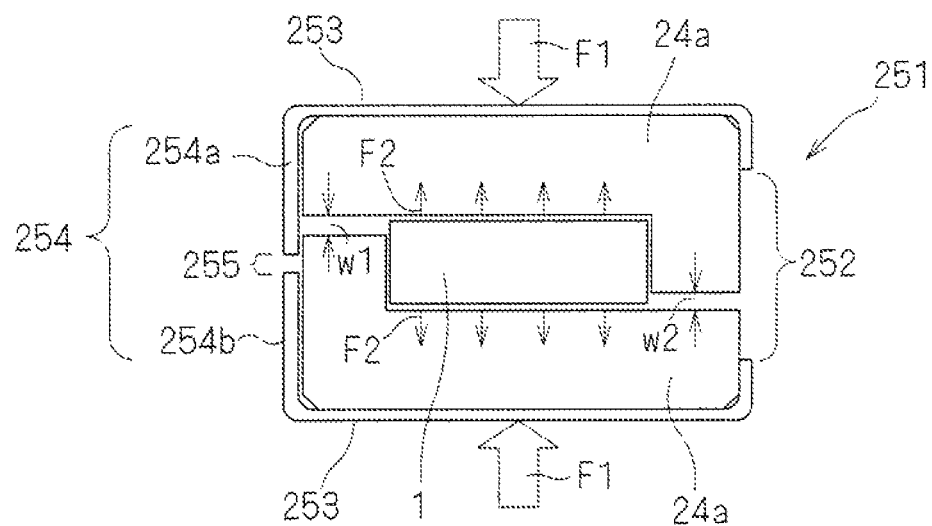
FIG. 9 is a cross-sectional view schematically showing the contact member 20 as taken along the line B-B' of FIG. 8.

FIG. 8 is a perspective view showing a main part of the fixture 25 according to this embodiment. FIG. 9 is a cross-sectional view schematically showing of the contact member 20 as taken along the line B-B' of FIG. 8, in a case where the contact member 20 configured using the fixture 25 according to this embodiment is clamped by the clamping ring 27.

Although not shown, in a case where the contact member 20 is configured using the fixture 25 according to this embodiment, similarly to the case of using the conventional fixture 1025, in a state before the clamping, the housing members 24a and the sensor element 1 are displaceable within a certain range though the housing members 24a and the sensor element 1 are restrained by the fixture 25.

Next, a case of clamping the clamping ring 27 will be considered. Firstly, in the second side portion 254, similarly to in the case of fixture 1025, the spaced portion 255 is narrowed to bring the upper side portion 254a and the lower side portion 254b closer to each other.

As for the first side portion 251, on the other hand, in the case of the fixture 25, the first side portion 251 is not continuous with the two upper and lower pressing surface portions 253 in a cross-sectional position passing through the opening 252 as shown in FIG. 9. Therefore, in the cross-sectional position, the compression force derived from the elastic force F1 does not act on the first side portion 251. The compression force acts only on the end edge portions 251a. Thus, most of the elastic force F1 concentrates on the end edge portions 251a. Therefore, the end edge portions 251a compressively deform without causing such a strong reaction force that is caused by the first side portion 251 of the conventional fixture 1025. The compressive deformation of the end edge portions 251a narrows the gap of the fist opening 252 in the vertical direction.

Thus, the fixture 25 is configured such that a vertical gap can be narrowed not only in the second side portion 254 having the spaced portion 255 but also in the first side portion 251 that is continuous with the pressing surface portion 253 and therefore receives the compression force from the upper and lower sides thereof when the elastic force F1 acts on the pressing surface portion 253 at a time of the clamping. In other words, the structure in which the opening 252 is provided in the first side portion 251 of the fixture 25 can be considered as a structure (reaction-force suppressing structure) that suppresses occurrence of a reaction force reactive to the compression force. The above-mentioned requirement that the area ratio of the opening 252 to the entire first side portion 251 should be 0.22 or more is defined as a requirement for suitably suppressing a reaction force in the first side portion 251 so that the gap can be narrowed in the vertical direction to a degree equal to the second side portion 254.

The end edge portions 251a of the first side portion 251 compressively deform in the above-described manner, and consequently the sensor element 1 is brought into contact with the contact-point members 21 provided to the housing members 24a, so that the sensor element 1 is contacted and fixed under pressure by the contact-point members 21. As described above, the end edge portions 251a are compressed with substantially no reaction force, so that, after the clamping, the first side portion 251 and the second side portion 254 shrink about the same degree from the pre-clamping state. Thus, the elastic force is substantially uniformly applied from the individual contact-point members 21 to the sensor element 1, and as a reaction thereof, the resistance force F2 is substantially uniformly applied from the sensor element 1 to the housing members 24a. That is, a uniform and stable contact state is established between the contact-point members 21 of the contact member and the electrode terminals 1a of the sensor element, and no slanted load occurs. Accordingly, the difference between the left and right opening degrees w1 and w2 of the two housing members 24a is also reduced as compared with the case of using the conventional fixture 1025.

From another viewpoint, after the clamping ring 27 is clamped, the fixture 25 substantially has the pressing surface portion 253 thereof merely sandwiched between the pressure springs 26 and the housing members 24a. That is, a state is established in which the elastic force F1 from the pressure springs 26 is directly applied to the housing members 24a irrespective of the restraint made by the fixture 25. This means that a restraint function of the fixture 25 is disabled after the clamping ring 27 is clamped.

As described above, in this embodiment, an opening is provided in the first side portion of the fixture which receives the compression force from the upper and lower sides thereof at the time of clamping, to thereby suppress occurrence of the reaction force reactive to the compression force. This can suppress occurrence of a slanted load in the contact-point members of the contact member, so that a uniform and stable contact state is established between the contact-point members of the contact member and the electrode terminals of the sensor element. As a result, electrical conduction between the sensor element and the contact member is stably ensured.

<Modifications>

In the above-described embodiment, the reaction-force suppressing structure causing substantially no reaction force in the first side portion at the time of clamping is achieved by providing the single opening 252 having a rectangular shape. However, an embodiment having the reaction-force suppressing structure is not limited to the above-described embodiment. Hereinafter, various modifications of the fixture having the reaction-force suppressing structure will be shown.

Figure 10:
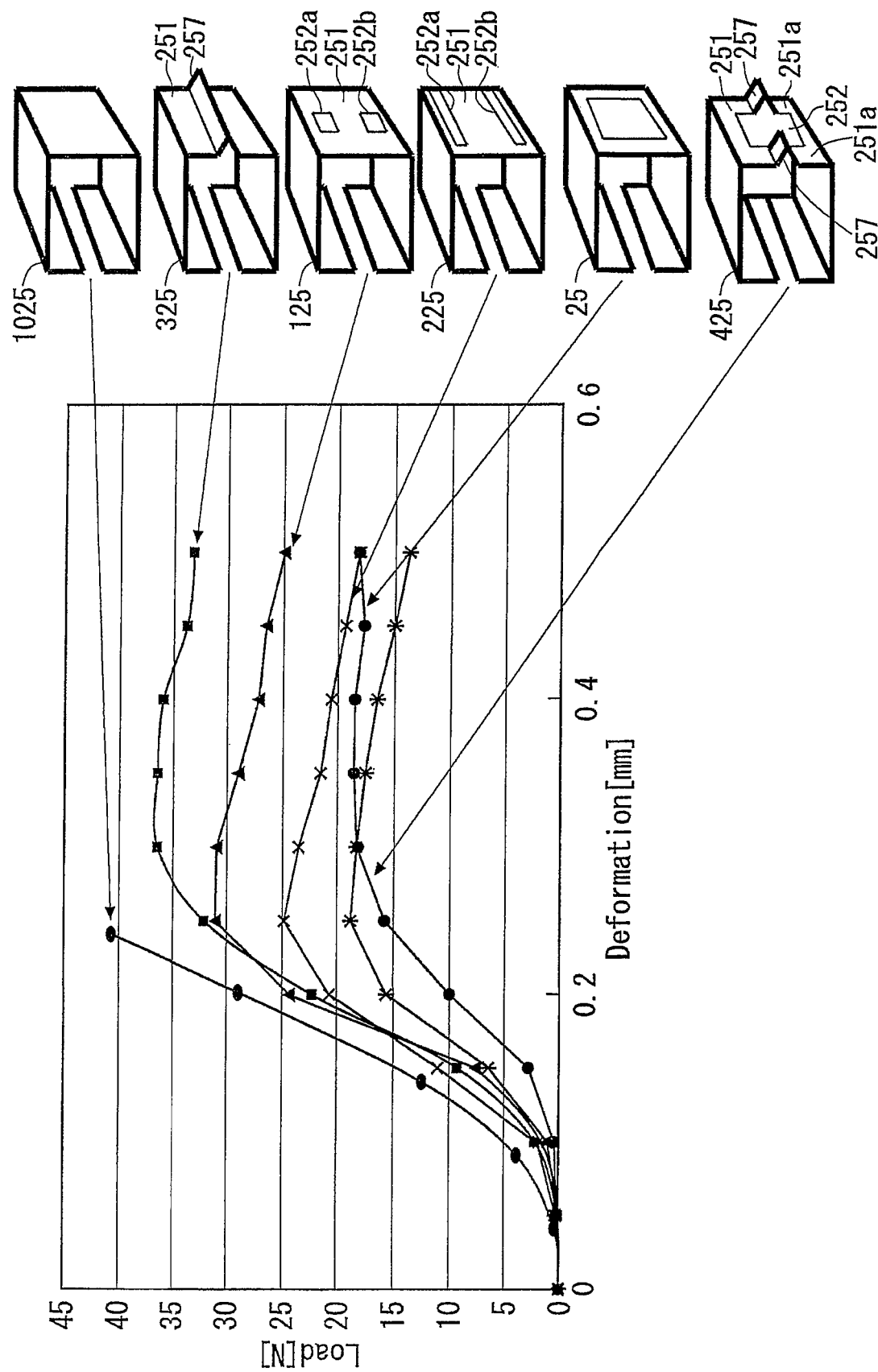
FIG. 10 is a diagram showing both perspective views of outline structures of fixtures according to modifications and deformation behaviors of the respective fixtures.

FIG. 10 is a diagram showing both perspective views of outline structures of fixtures 125, 225, 325, and 425 according to modifications and deformation behaviors (Load-Deformation Curves) of the respective fixtures with respect to a load. Any of the fixtures 125, 225, 325, and 425 has a configuration identical to that of the fixture 25 according to the above-described embodiment, except that the shape of the first side portion 251 is different. In FIG. 10, for comparison, the fixture 25 according to the above-described embodiment and the conventional fixture 1025 are also shown.

FIG. 11 is a diagram schematically showing measurement of the deformation behavior of each of the fixtures shown in FIG. 10. In FIG. 11, a case where the fixture 325 is to be measured is shown as an example. The deformation behavior is obtained by measuring the amount of deformation of the first side portion 251 at a time of, while placing the fixture on a predetermined stage 51, applying a load 52 from the upper side of the first side portion 251. In this measurement, the spaced portion 255 of the second side portion 254 is fixed by a fixing member 53. Therefore, a measurement result shown in FIG. 10 is different from a deformation behavior obtained when the clamping performed while the fixture is actually assembled. However, since measurement conditions are the same with respect to all of the fixtures, whether the reaction-force suppressing structure in the first side portion 251 is relatively good or not can be determined based on the result shown in FIG. 10.

Each of the fixture 125 and the fixture 225 has two openings 252a and 252b at the first side portion 251. In these fixtures 125 and 225, too, the openings 252a and 252b are provided such that a ratio of the total opening area to the entire first side portion 251 is not less than 0.22. Thereby, similarly to the above-described embodiment, the reaction force can be suitably suppressed in the first side portion 251 at the time of clamping.

The fixture 325 has no opening, and instead, has a bent portion 257 that is formed by folding a part of the first side portion 251 so as to protrude outwardly. In a case where the fixture 325 configured in such a manner is used in the contact member 20, the compression force acting on the first side portion 251 from the upper and lower sides thereof at the time of clamping is absorbed by the bent portion 257 shrinking in the vertical direction (compressively deforming). Thereby, the reaction force reactive to the compression force is suppressed.

The fixture 425 is configured so as to have both of the opening 252 and the bent portion 257. In a case where the fixture 425 is used in the contact member 20, the compression force acting on the first side portion 251 from the upper and lower sides thereof at the time of clamping is absorbed by both the opening 252 and the bent portion 257. Thereby, the reaction force reactive to the compression force is suppressed.

Referring to FIG. 10, in the cases of the fixtures 25, 125, 225, 325, and 425, the value of a load reaches saturation at approximately 37 N at the maximum, while in the case of the conventional fixture 1025, the value does not reach saturation even at 40 N or more. This means that the compressive deformation of the fixtures 25, 125, 225, 325, and 425 is caused by a smaller load as compared with the conventional fixture 1025. Thus, the result suggests that the fixtures 25, 125, 225, 325, and 425 have a good compression-force absorbing structure

EXAMPLES

Example 1

In an example 1, an NOx sensor was prepared by integrating the contact member 20 including the fixture 25 according to the above-described embodiment with the gas sensor main body 10, and thereafter, it was disassembled and heights h of the protrusions 21d of all the contact-point members 21 used in the contact member 20 were measured. The number of measured protrusions 21d was set to be 232 (the number of measured sensors was set to be 29). FIG. 12 is a diagram showing the height h of the protrusion 21d that was a measurement object.

In a comparative example, using a contact member that includes the fixture 1025 having the same structure as that of the fixture 25 according to the example except that the opening 252 is not provided, an NOx sensor was prepared and then the subsequent disassembling and measurement were performed similarly to the example. The number of measured protrusions 21d was 232 (the number of measured sensors was 29).

Figure 13:
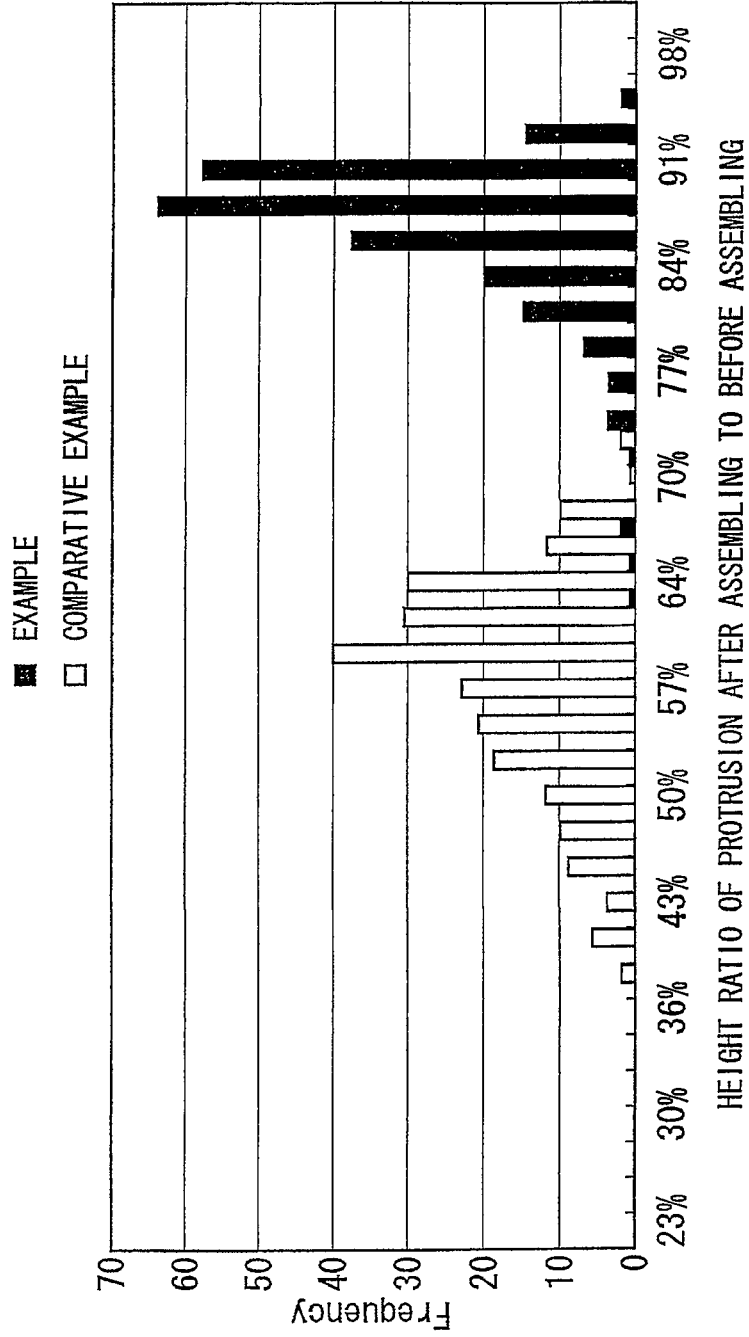
FIG. 13 is a histogram showing a ratio of the height h to an initial value that was obtained before assembling with respect to an example and a comparative example.

FIG. 13 is a histogram showing a ratio of the height h to an initial value (fixed value) that was obtained before assembling with respect to the example and the comparative example. Referring to a result shown in FIG. 13, the value is more uniform in the example than in the comparative example. The histogram of FIG. 13 includes all measurement results concerning the contact-point members 21 assembled at different locations in the contact member 20. Therefore, the above-described result indicates that a force acting on the contact-point members 21 assembled at different locations in the contact member 20 is more uniform in the example than in the comparative example.

Additionally, referring to FIG. 13, representative values (the median, the average, the mode) of a distribution are greater in the example than in the comparative example. Therefore, it can be considered that, generally, the degree of plastic deformation of the protrusion 21d is lower in the example than in the comparative example. This result means that fixing of the sensor element can be performed with a smaller force in the example than in the comparative example. This is because in the comparative example, it was necessary to apply an extra force in order to counteract a reaction force occurring in the first side portion 251 of the fixture 1025 at a time of fixing the sensor element, while in the example, a compression force occurring at a, time of clamping was absorbed so that a reaction force hardly occurred, and therefore it was not necessary to apply an extra force.

Example 2

Figure 14:
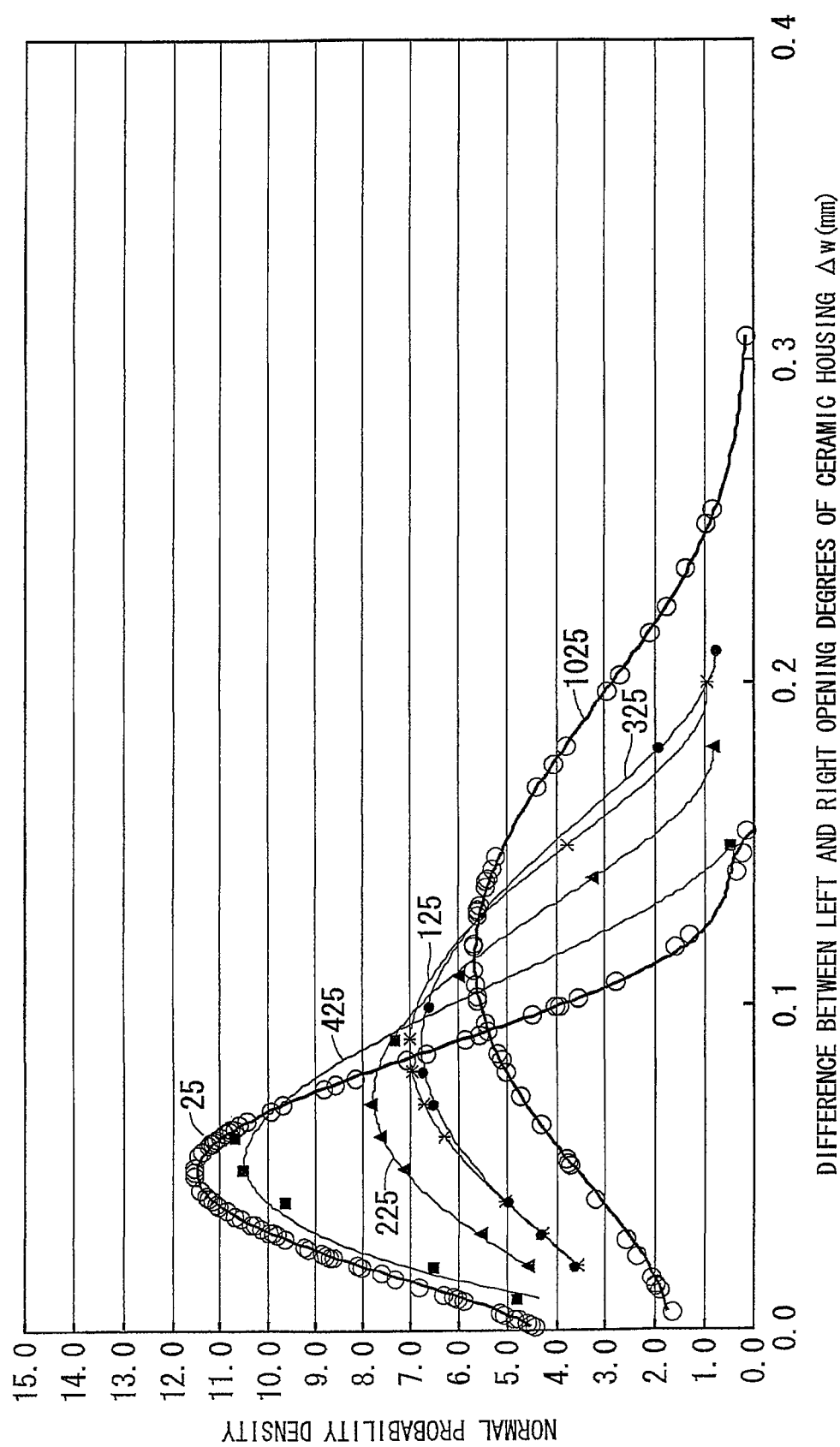

In an example 2, a plurality of fixtures 25, a plurality of fixtures 125, a plurality of fixtures 225, a plurality of fixtures 325, a plurality of fixtures 425, and a plurality of fixtures 1025 were prepared, and the contact member 20 was integrated with the gas sensor main body 10 to thereby prepare an NOx sensor. Then, the difference Δw=w2−w1 between the left and right opening degrees w1 and w2 of the housing members 24a was measured. The number of measured fixtures 25 was 90. The number of measured fixtures 125 was 11. The number of measured fixtures 225 was 11. The number of measured fixtures 325 was 11. The number of measured fixtures 425 was 11. The number of fixtures 1025 was 50. FIG. 14 is a diagram showing normal probability density curves of Δw obtained based on results of these measurement. In FIG. 14, each of the curves is signed with the reference numeral of the corresponding fixture.

Referring to FIG. 14, in all of the fixtures 25, 125, 225, 325, and 425 having the compression-force absorbing structures, the distribution of Δw was closer to 0 than the conventional fixture 1025 was. This tendency was particularly significant in the fixtures 25 and 425. Such a result reveals that the sensor element is fixed more uniformly by using the fixtures 25, 125, 225, 325, and 425 than by using the fixture 1025.

The invention claimed is:

1. A contact member for a gas sensor configured to fix a sensor element by sandwiching said sensor element in an insertion port defined by a pair of housing members to thereby obtain electrical connection with said sensor element, said contact member comprising:
    a restraint member provided at an outer circumference of said pair of housing members, said restraint member having a restraint function for restraining a displacement of said pair of housing members within a predetermined range; and
    an annular member provided at an outer circumference of said restraint member,
wherein
    a compression force, which occurs when said annular member shrinkingly deforms by receiving an external force with said sensor element inserted in said insertion port, is applied through said restraint member to thereby contact said pair of housing members with said sensor element under pressure, so that said sensor element is fixed by being sandwiched between said pair of housing members in a state that an electrode terminal provided on said sensor element and a contact-point member provided on said pair of housing members are in contact with each other,
    said restraint member comprises:
        two pressing surface portions to which the compression force that occurs when said annular member shrinkingly deforms is applied;
        a first side portion coupled perpendicularly to said two pressing surface portions; and
        a second side portion having an upper side portion coupled perpendicularly to one of said two pressing surface portions and a lower side portion coupled perpendicularly to the other of said two pressing surface portions, said second side portion also having a spaced portion provided between said upper side portion and said lower side portion,
    said first side portion has a reaction-force suppressing structure for suppressing occurrence of a reaction force reactive to said compression force.

2. The contact member for a gas sensor according to claim 1, wherein
    said first side portion has at least one opening, and said reaction force is suppressed by causing an end edge portion located lateral to said opening to compressively deform due to said compression force.

3. The contact member for a gas sensor according to claim 1, wherein
    said first side portion has a bent portion, and said reaction force is suppressed by causing said bent portion to compressively deform due to said compression force.

4. The contact member for a gas sensor according to claim 1, wherein
    said first side portion has at least one opening and also has a bent portion formed at an end edge portion located lateral to said opening, and said reaction force is suppressed by causing said end edge portion including said bent portion to compressively deform.

\* \* \* \* \*